(12) United States Patent
Fukumoto et al.

(10) Patent No.: US 6,232,473 B1
(45) Date of Patent: May 15, 2001

(54) PROCESS FOR PRODUCING 2-AZABICYCLO[2.2.1]HEPT-5-EN-3-ONE

(75) Inventors: Takashi Fukumoto; Rensuke Ikarashi, both of Kitakanbara-gun (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 09/562,129

(22) Filed: May 1, 2000

(30) Foreign Application Priority Data

Apr. 30, 1999 (JP) .................................................. 11-124015

(51) Int. Cl.$^7$ .................................................. C07D 209/52
(52) U.S. Cl. .................................................. 548/512
(58) Field of Search .................................................. 548/512

(56) References Cited

U.S. PATENT DOCUMENTS

| | | | |
|---|---|---|---|
| 5,200,527 | 4/1993 | Griffiths et al. | 548/452 |
| 5,300,649 | 4/1994 | Griffiths et al. | 546/290 |
| 5,847,157 | 12/1998 | Romanowski et al. | 548/512 |
| 6,060,609 | 5/2000 | Fukumoto et al. | 548/512 |

FOREIGN PATENT DOCUMENTS

| | | |
|---|---|---|
| 5-331139 | 12/1993 | (JP) . |
| 5-331140 | 12/1993 | (JP) . |
| 8-27110 | 1/1996 | (JP) . |
| 9-165372 | 6/1997 | (JP) . |

OTHER PUBLICATIONS

J. C. Jagt, et al., J. Org. Chem., vol. 39, No. 4, pp. 564 to 566, "Diels–Alder Cycloadditions of Sulfonyl Cyanides with Cyclopentadiene. Synthesis of 2–Azabicyclo[2.2.1]Hepta–2,5–Dienes", 1974.

S. Daluge, et al., J. Org. Chem., vol. 43, No. 12, pp. 2311–2320, "Synthesis of Carbocyclic Aminonucleosides", 1978.

B. L. Kam, et al., J. Org. Chem., vol. 46, No. 16, pp. 3268 to 3272, "Carbocyclic Sugar Amines: Synthesis and Stereochemistry of Racemic α–and β–Carbocyclic Ribofuranosylamine, Carbocyclic Lyxofuranosylamine, and Related Compounds", 1981.

W. C. Faith, et al., J. Org. Chem., vol. 50, No. 11, pp. 1983 to 1985, "An Approach to the Synthesis of Neplanocin A", 1985.

G. J. Griffiths, et al., J. Org. Chem., vol. 58, No. 22, pp. 6129 to 6131, "Diels–Alder Reaction of Methanesulfonyl Cyanide with Cyclopentadiene. Industrial Synthesis of 2–Azabicyclo[2.2.1]Hept–5–en–3–One", 1993.

J. R. Malpas, et al., J. C. S. Perkin I, pp. 874 to 884, "Reaction of Chlorosulponyl Isocyanate with 1,3–Dienes. Control of 1,2–and 1,4–Addition Pathways and the Synthesis of Aza–and Oxa–Bicyclic Systems", 1977.

N. Katagiri, et al., Chem. Pharm. Bull., vol. 44, No. 4, pp. 850 to 852, "Hetero Diels–Alder Reaction of Benzenesulfonyl Cyanide with Cyclopentadiene Using Chiral Lewis Acids", 1996.

Primary Examiner—Fiona T. Powers
(74) Attorney, Agent, or Firm—Oblon, Spivak, McClelland, Maier & Neustadt, P.C.

(57) ABSTRACT

2-Azabicyclo[2.2.1]hept-5-en-3-one is prepared by a process comprising:

continuously mixing a substituted sulfonyl cyanide represented by formula (I):

$$R-SO_2CN \qquad (I),$$

wherein R represents an alkyl group or a phenyl group or a substituted phenyl group, with cyclopentadiene; and then continuously adding the resultant reaction solution to water or to a mixed solvent comprising water and a hydrocarbon solvent under the condition that the pH of the present reaction mixture ranges from 4 to 7.

14 Claims, No Drawings

PROCESS FOR PRODUCING 2-AZABICYCLO[2.2.1]HEPT-5-EN-3-ONE

BACKGROUND OF THE INVENTION

1. Field of the Invention

The present invention relates to a process for producing 2-azabicyclo[2.2.1]hept-5-en-3-one (ABH), which is an intermediate in the synthesis of carbocyclic nucleosides that are useful as medicinal agents such as anti-virus agents.

2. Description of the Background

Since carbocyclic nucleosides have a structure in which the oxygen atom of the furanose ring of the nucleoside is substituted with a methylene group and the structure is very similar to a natural nucleoside having a furanose ring, these molecules can act as substrates or inhibitors for various enzymes in living bodies. Further, since the carbocyclic nucleoside has no glycoside bonding, the compound can not be cleaved or split by enzymes such as nucleoside phospholylases and nucleoside hydrases. Since they have different metabolic pathways from natural nucleosides having the furanose ring, they exhibit various physiological activities. For example, carbocyclic adenosine known as Aristeromycin is a sort of carbocyclic nucleoside, which is a metabolite of *Streptomyces citricolor* and has been noted for its strong cytotoxicity which is different from nucleosides having the furanose ring.

Further, carbocyclic-2,3-dideoxy-2,3-didehydroguanosine, as a sort of carbocyclic nucleoside, has now been developed as an anti-HIV agent (R. Vince et al., Biochem, Biophys. Res. Commun. 156, 1046 (1988)).

ABH is a compound that is most frequently used as an intermediate for the pure chemical synthesis of the carbocyclic moiety of these carbocyclic nucleosides, such as 2 α, 3 α-dihydroxy-4 β-aminocyclopentanone-1 β-methanol and cis-4-aminocyclopent-2-en-1 β-methanol (R. Vince, et al., J. Org. Chem., 43, 2311 (1978); B. L. Kamm et al., J. Org. Chem., 46, 3268 (1981); W. C. Faith et al., J. Org. Chem., 50, 1983 (1985)).

A method of synthesis of ABH is known in which cyclopentadiene and p-toluenesulfonyl cyanide are subjected to a cycloaddition reaction to form 3-p-toluenesulfonyl-2-azabicyclo[2.2.1]hepta-2,5-diene as an intermediate and then removing the toluenesulfonyl group on the 3-position of the intermediate by using acetic acid (J. C. Jagt et al., J. Org. Chem., 39, 564 (1974); R. Vince et al., J. Org. Chem., 43, 2311 (1978)).

However, the process of synthesis process described above has various problems, for example, in that ① cyclopentadiene which may be used theoretically in an equimolar amount to p-toluenesulfonyl cyanide has to be actually used in a greatly excess amount of 15 to 35 molar times; ② 3-p-toluenesulfonyl-2-azabicyclo[2.2.1]hepta-2,5-diene obtained by the reaction of p-toluenesulfonyl cyanide and cyclopentadiene has to be condensed and removed as lumps from the reaction medium, which then must be pulverized into powder and then reacted with acetic acid; ③ acetic acid has to be added in a greatly excess amount of 5 to 23 molar times, all at once in order to remove the toluenesulfonyl group at the 3-position by treating 3-p-toluenesulfonyl-2-azabicyclo[2.2.1]hepta-2,5-diene with acetic acid, so that an abrupt exothermic reaction has to be controlled; ④ if the exothermic reaction of item ③ cannot be controlled satisfactorily and the reaction temperature rises excessively, the desired product, ABH, cannot be obtained at all or is obtainable only in extremely low yields, ⑤ solid by-products are formed upon the reaction in the ③, which hinder smooth stirring and the reaction does not proceed smoothly; and ⑥ a great amount of waste water is formed which increases the burden for treating the same. Therefore, ABH cannot be produced satisfactorily industrially by the synthesis process described above, from the viewpoint of economy and safety.

Under the circumstances described above, effort has now been made to develop a process which is capable of producing ABH in a high purity and a high yield with safety and in good productivity by reacting a sulfonyl cyanide such as p-toluenesulfonyl cyanide with cyclopentadiene under conditions which permit the use of a reduced amount of the reagent and solvent to be used. Previous effort in this area has already produced results, with patent applications having been filed which describe these efforts:

(i) A process for producing ABH by way of a first step of condensing sulfonyl cyanide and cyclopentadiene in a hydrocarbon solvent and then treating the product obtained with water (Japanese Published Unexamined Patent Application No. Hei 5-331139);

(ii) A process for producing ABH by reacting sulfonyl cyanide and cyclopentadiene in water or in a mixed solvent of water and a hydrocarbon (Japanese Published Unexamined Patent Application No. Hei 5-331140);

(iii) A process for producing ABH by reacting benzenesulfonyl cyanide and cyclopentadiene in a mixed solvent of water and a water soluble solvent under pH conditions ranging from 3 to 4 (Japanese Published Unexamined Patent Application No. Hei 8-27110); and (iv) A process for producing ABH by reacting sulfonyl cyanide and cyclopentadiene in a hydrocarbon solvent to form 3-sulfonyl-2-azabicyclo[2.2.1]hepta-2,5-diene as an intermediate product and hydrolyzing the intermediate product by adding a solution of the intermediate product into a mixed solvent of water and a water soluble solvent at a pH ranging from 3 to 7 (Japanese Published Unexamined Patent Application No. Hei 9-165372).

When compared with the existing process described by J. C. Jagt et al. in which ABH is prepared by reacting acetic acid with 3-p-toluenesulfonyl-2-azabicyclo[2.2.1]hepta-2,5-diene prepared in turn by the reaction of cyclopentadiene and p-toluenesulfonyl cyanide, the procedures (i)–(iv) described above have various advantages including that:

(a) it is not necessary to use cyclopentadiene in a great excess relative to sulfonyl cyanide;

(b) no troublesome procedure or effort needs to be expended to remove 3-p-toluenesulfonyl-2-azabicyclo [2.2.1]hepta-2,5-diene, which is formed as the intermediate product in a condensed form, pulverizing the same into powder, and then subjecting the powder to a succeeding process step;

(c) since no abrupt exothermic reaction takes places, control of the reaction is easy and results in increased safety;

(d) the yield of the desired product ABH is high;

(e) solid by-products which hinder the stirring during the reaction are formed in comparatively lesser amounts; and (f) the amount of waste water to be treated is small which moderates the processing burden.

Each of the processes (i) and (iv) above is conducted by way of two steps of reacting sulfonyl cyanide and cyclopentadiene in a hydrocarbon solvent in the first step to form 3-sulfonyl-2azabicyclo[2.2.1]hepta-2,5-diene as an intermediate product and then processing the solution of the intermediate product in water in the process (i) or a mixed solvent of water and a water soluble solvent in the process (iv) in the second step to produce ABH.

In these processes, however, it is necessary to handle 3-sulfonyl-2-azabicylo[2.2.1]hepta-2,5-diene, which is relatively unstable. In view of this constraint, room for improvement remains.

On the other hand, each of the processes (ii) and (iii) above is a process by which ABH can be directly produced by reacting sulfonyl cyanide and cyclopentadiene in water or a mixed solvent of water and a hydrocarbon solvent or in a mixed solvent of water and a water soluble solvent in one step. This process is simpler than the two step processes (i) or (iv) above and can be said to be industrially advantageous.

In method (ii), the pH is not controlled during the reaction of sulfonyl cyanide and cyclopentadiene, and it has been found that the pH of the reaction mixture is 3 or less, generally pH 2 to 3, because of the presence of sulfonyl cyanide in the mixture or a sulfinic acid such as, for example, benzenesulfinic acid, which is formed by the reaction. Because of this fact it is difficult to completely prevent deposition of material from the reaction mixture, of solid products such as dimerization products of sulfinic acid such as benzenesulfinic acid, of the likes of, for example, benzenesulfinyl sulfone, which results from the reaction of sulfonyl cyanide and cyclopentadiene, for example, and thus a filtration step for the deposited solid products is required. If deposition of the solid products is to be prevented completely, a great amount of water or hydrocarbon solvent has to be used, which increases the burden on waste water treatment, which leaves room for improvement in the process.

Further, in method (iii) above, sulfonyl cyanide and cyclopentadiene react at a pH ranging from 3 to 4 and it is difficult to completely prevent deposition of dimerization products of a sulfinic acid such as benzenesulfinic acid, of the likes of benzenesulfinyl sulfone, for example, perhaps because a mixed solvent of water and a water-soluble solvent is used as a solvent. Moreover, method (iii) gives a lower yield of ABH than process (ii) described above. A need, therefore, continues to exist for improvement in ABH synthesis.

SUMMARY OF THE INVENTION

Accordingly, one object of the present invention is to provide a method of ABH synthesis by the reaction of substituted sulfonyl cyanide and cyclopentadiene which is safe and which provides for the production of ABH economically in high purity and high yield.

Briefly, this object and other objects of the present invention as hereinafter will become more readily apparent can be attained by a process for producing a 2-azabicyclo[2.2.1]hept-5-en-3-one by continuously mixing a substituted sulfonyl cyanide represented by formula (I):

$$R-SO_2CN \qquad (I)$$

wherein R represents an alkyl group or a phenyl group which may be substituted with cyclopentadiene, and continuously adding the resultant reaction solution to water or a mixed solvent comprising water and a hydrocarbon solvent under the condition that the pH of the present reaction mixture ranges from 4 to 7.

DETAILED DESCRIPTION OF THE PREFERRED EMBODIMENTS

Effort has now been made to provide an improved process for smoothly producing ABH in high purity on an industrial scale. As a result, it has now been found that by continuously mixing sulfonyl cyanide and cyclopentadiene, thereby producing 3-sulfonyl-2-azabicyclo[2.2.1]hepta-2,5-diene as an intermediate, and then continuously adding this reaction solution dropwise to water or a mixed solvent of water and a hydrocarbon solvent while keeping the pH always within the range of 4 to 7 during the reaction by the addition of an alkali to the reaction mixture, the time over which unstable 3-sulfonyl-2-azabicyclo[2.2.1]hepta-2,5-diene exists can be shortened to produce the desired ABH in high purity and high yield, thereby increasing industrial safety and achieving good productivity. It has also been found that even if the amount of the water and hydrocarbon solvent to be used is reduced in the control of the pH of the reaction mixture within the range of 4 to 7 during the above-mentioned reaction, the reaction can proceed without precipitation of any solid dimerization products of sulfinic acid such as benzenesulfinic acid, of the likes of benzenesulfinyl sulfone and that in this case any problems such as the impossibility of stirring during the reaction do not occur at all and the step of filtering the solution can be omitted. These advantages are significant.

In the substituted sulfonyl cyanide reactant of formula (I) of the present process (hereinafter referred to as sulfonyl cyanide (I)), R represents an alkyl group or a phenyl group with or without a substituent. The alkyl group is preferably an alkyl group of from 1 to 4 carbon atoms, specifically, methyl, ethyl, n-propyl, i-propyl, n-butyl, i-butyl or t-butyl. The phenyl group is preferably a nonsubstituted phenyl group or a substituted phenyl group represented by formula (II):

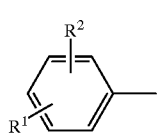

(II)

wherein $R^1$ and $R^2$ each independently represents a hydrogen atom, an alkyl group or a halogen atom.

In formula (II), when $R^1$ and/or $R^2$ is an alkyl group, it is preferably an alkyl group of from 1 to 4 carbon atoms, more preferably methyl or ethyl. Further, if $R^1$ and/or $R^2$ is a halogen atom, the atom is preferably chlorine, bromine or fluorine.

In the sulfonyl cyanide (I), group R is preferably methyl, ethyl, phenyl group or p-tolyl and, thus, in the present invention, methanesulfonyl cyanide, ethanesulfonyl cyanide, benezenesulfonyl cyanide, p-toluenesulfonyl cyanide or a mixture of two or more of these compounds is used preferably as the sulfonyl cyanide (I), and benzenesulfonyl cyanide, p-toluenesulfonyl cyanide or a mixture thereof is used more preferably.

The process by which embodiments of sulfonyl cyanide compound (I) of the present invention is produced is not particularly limited, and it may be produced by any known method. In addition, the purity of the sulfonyl cyanide (I) to be used in the present invention is not particularly limited, but compounds having a purity of 70% or higher are generally, preferably used, since the desired ABH compound can be obtained smoothly.

The process for producing cyclopentadiene as a co-reactant in the present invention is not particularly limited, and it may be produced by any known method. In addition, there is no particular restriction on the purity of cyclopentadiene. Among them, use of cyclopentadiene formed by thermal decomposition of dicyclopentadiene just after the preparation is preferred, since the content of impurity is small, and post-treatment of ABH after its production is easy.

In the process of the present invention, cyclopentadiene is preferably used in an amount of at least one mol. per mol. of sulfonyl cyanide (I). Preferably, from 1 to 5 mols. of cyclopentadiene is used per one mol. of sulfonyl cyanide (I), particularly, in view of economy of the reaction and ease of post-treatment processing.

When mixing sulfonyl cyanide (I) and cyclopentadiene, it is possible to mix the compounds in a solvent. The solvent is not limited as long as it is inert to the cycloaddition reaction of sulfonyl cyanide (I) and cyclopentadiene. Suitable solvents include aliphatic and aromatic hydrocarbons such as pentane, hexane, heptane, benzene, toluene, xylene; chlorinated hydrocarbons such as methylene chloride, chloroform and dichlorobenzene; ketones such as acetone, methyl isopropyl ketone and methyl isobutyl ketone; ethers such as diethyl ether, diisopropyl ether and methyl t-butyl ether. If these solvents are used, they may be used alone or as a mixture of two or more. In general, the weight of the solvent to be used preferably ranges from 0.1 to 20 parts by weight, more preferably from 0.1 to 5 parts by weight based on one part by weight of sulfonyl cyanide (I), from the viewpoint of economy.

The temperature while mixing sulfonyl cyanide (I) and cyclopentadiene is preferably within the range of 0 to 50° C. From the viewpoint of stability of 3-sulfonyl-2-azabicyclo [2.2.1]hepta-2,5-diene, which is an intermediate, the temperature is more preferably within the range of 0 to 30° C.

One method for mixing sulfonyl cyanide (I) and cyclopentadiene is to supply sulfonyl cyanide (I) and cyclopentadiene simultaneously to a mixing apparatus. If a solvent is used, the solvent may be in a state in which the solvent is blended with only one or both of sulfonyl cyanide (I) and cyclopentadiene. The mixing apparatus may be any known apparatus such as a stirring type reaction vessel or a tube type reaction vessel. In order to add the reaction solution obtained by continuously mixing sulfonyl cyanide (I) and cyclopentadiene in water or in a mixed solvent of water and a hydrocarbon solvent, the mixing apparatus is connected to a reaction vessel wherein water or the mixed solvent of water and the hydrocarbon solvent is charged, in the manner that the prepared reaction solution can be continuously sent to the reaction vessel.

The residence time for mixing sulfonyl cyanide (I) and cyclopentadiene may vary depending on the temperature upon mixing or, if a solvent is used together, the kind of solvent. The residence time is usually within the range of 5 to 600 minutes, preferably within the range of 5 to 120 minutes, and more preferably, within the range of 10 to 90 minutes from the viewpoint of the yield of the desired ABH product. If the residence time is less than 5 minutes, the cycloaddition reaction of sulfonyl cyanide (I) and cyclopentadiene tends to proceed insufficiently, so that the yield of ABH decreases. If the residence time exceeds 600 minutes, 3-sulfonyl-2-azabicyclo[2.2.1]hepta2,5-diene, which is an intermediate produced by the cycloaddition reaction, tends to decompose with the result that the yield of ABH decreases.

Subsequently, the thus prepared reaction solution of sulfonyl cyanide (I) and cyclopentadiene is continuously added to water or a mixed solvent of water or a hydrocarbon solvent which is to be subjected to hydrolysis.

The amount of water to be used usually ranges from 1 to 200 parts by mol., preferably from 1 to 50 parts by mol. based on one mol. of the sulfonyl cyanide (I), in view of ease of post-treatment processing.

Suitable Examples of the hydrocarbon solvent include aliphatic or aromatic hydrocarbons such as pentane, hexane, heptane, benzene, toluene, xylene and the like. These may be used alone or as a mixture of two or more. When the hydrocarbon solvent is used, the weight thereof is preferably within the range of 0.005 to 200 parts by weight, and more preferably, within the range of 0.01 to 50 parts by weight based on one part by weight of water from the viewpoint of economy.

In the present invention, it is important that when adding the reaction solution of the sulfonyl cyanide (I) and cyclopentadiene continuously to water or a mixed solvent of water and a hydrocarbon solvent, the pH of the reaction mixture is constantly observed in the manner that the pH of the reaction mixture is kept within the range of 4 to 7. If the pH of the reaction mixture is less than 4, solid products such as dimerization products of sulfinic acid, such as for example, benzenesulfinic acid, or the likes of benzenesulfinyl sulfone are deposited from the reaction mixture, which makes stirring difficult during the reaction. Further, a filtration step for the separation the solid products is required which makes the reaction step complicated and lowers the yield and the purity of ABH. On the other hand, if the pH of the reaction mixture exceeds 7, hydrolysis of the resultant ABH proceeds which decreases the yield. In the present invention, the pH of the reaction mixture is preferably kept within the pH range of 4 to 6.5, more preferably a pH of 4.2 to 5.5 in order to prevent the deposition of the solid materials, and preventing hydrolysis of the resultant ABH.

A preferred method of keeping the pH of the reaction mixture within the range of 4 to 7, is a method of optionally adding one or more of organic or inorganic alkali compounds, which do not hinder the reaction, to the reaction mixture while always observing the pH of the reaction mixture. In particular, the pH is preferably kept within the range of 4 to 7 by adding an aqueous solution of one or more inorganic alkali compounds such as alkali metal hydroxides, for example, sodium hydroxide and potassium hydroxide; alkaline earth metal hydroxides, for example, calcium hydroxide, magnesium hydroxide and barium hydroxide; alkali metal carbonates, for example, sodium carbonate and potassium carbonate; alkaline earth metal carbonates, for example, calcium carbonate, magnesium carbonate and barium carbonate; alkali metal bicarbonates, for example, sodium hydrogen carbonate and potassium hydrogen carbonate, to the reaction mixture since the pH can be controlled easily.

The hydrolysis reaction is preferably conducted within the range of 0 to 50° C., more preferably within the range of 5 to 30° C. in view of the stability of the product ABH in the reaction mixture.

The hydrolysis reaction is preferably conducted with stirring, so that the reaction can proceed smoothly. The reaction time can be controlled depending on the kind of sulfonyl cyanide (I), the amounts of sulfonyl cyanide (I) and cyclopentadiene and the ratios thereof to be used, the amount of the hydrocarbon solvent and water to be used, the reaction temperature, the scale of the reactor, and the like. It is generally preferred to conduct the hydrolysis reaction for a time within the range of 30 minutes to 48 hours including the addition time (dropping time) of the reaction solution of the sulfonyl cyanide (I) and cyclopentadiene. The reaction may be conducted batchwise or continuously.

As described above, the hydrolysis reaction is conducted while maintaining the pH of the reaction mixture to within the range of 4 to 7, so as to produce the desired ABH product. Thereafter, the reaction can be terminated by controlling the pH of the reaction mixture which exceeds 7 and is 8 or lower.

The reaction mixture which contains ABH obtained as described above can be used without isolating ABH from the reaction mixture, as a starting material for synthesizing carbocyclic nucleoside or the like. However, ABH is preferably isolated from the reaction mixture.

The method for isolating ABH from the reaction mixture is not particularly limited, and any method can be used as long as it is a method which is capable of isolating ABH smoothly. A preferred method of isolating ABH from the reaction mixture is one which: extracts the reaction mixture with an appropriate extraction solvent in the case that only water is used, or separating the reaction mixture into an aqueous layer and a hydrocarbon solvent layer, recovering the aqueous layer and extracting ABH contained in the aqueous layer by an appropriate extraction solvent in the case that the mixed solvent of water and the hydrocarbon solvent; and then distilling the extraction solvent to give the desired ABH product, by which the ABH can be obtained in high yield and high purity. As the extraction solvent in this case, any solvent can be used as long as it is a solvent which is capable of extracting ABH from the aqueous layer, but a chlorinated hydrocarbon solvent such as methylene chloride, chloroform or dichloroethane is preferably used.

In the method of isolation as described above, if the extraction treatment by the extraction solvent is conducted after passing the aqueous layer containing ABH through an activated carbon packed column or charging activated carbon in the aqueous layer to remove impurities such as oily products derived from cyclopentadiene contained in the aqueous layer, before the extraction treatment of the aqueous layer by the extraction solvent, ABH in a higher purity can be obtained. Among them, the method of passing the aqueous layer containing ABH through the activated carbon packed column is extremely effective for removing impurities. The kind of the activated carbon to be used for the removal of the impurities is not particularly limited, but any activated carbon can be used and, among them, KURARAY COAL GC-F (manufactured by Kuraray Chemical Co., Ltd.) is preferably used. The shape, the structure and the size of the activated carbon packed column are not particularly limited, and can be determined depending on situations.

ABH obtained as described above, has a sufficiently high purity as such, and can be used effectively as a material for synthesizing a carbocyclic nucleoside or the like, but it can be further purified or made easily handleable by optionally conducting an additional distillation, activated carbon-treatment, sublimation or recrystallization.

In the isolating step described above, a sulfinate of the formula R—$SO_2$M, wherein M represents a salt-forming cation, remains in the aqueous layer after isolating ABH by conducting extraction, for example, with a chlorinated hydrocarbon solvent. If cyanogen chloride is added to the aqueous layer containing sulfinate after the extraction treatment, since sulfinate is easily converted to sulfonyl cyanide (I), the sulfonyl cyanide (I) produced by the conversion may be reutilized as a starting material for producing ABH.

According to the present invention, 2-azabicyclo[2.2.1] hept-5-en-3-one can be safely and economically produced in high purity and high yield. Since the amounts of water and the hydrocarbon solvent to be used can be reduced, the burden of treating waste water is substantially alleviated.

Having now generally described this invention, a further understanding can be obtained by reference to certain specific Examples which are provided herein for purposes of illustration only and are not intended to be limiting unless otherwise specified.

EXAMPLES

Reference Example 1
<Synthesis of benzenesulfonyl cyanide>

In a 200 ml four-necked flask, 70 g of water, 2 g of methylene chloride and 32.0 g (0.16 mol.) of sodium benzenesulfinate dihydrate were charged, and then cooled to 3° C. Then, 10.7 g (0.17 mol.) of gaseous cyanogen chloride was introduced into the flask for about 15 minutes while keeping the internal temperature at 3 to 6° C. After introducing cyanogen chloride, the reaction mixture was stirred at 5° C. for 30 minutes and then the mixture was transferred into a separation funnel. The organic layer was separated, and 5 g of methylene chloride was added to the aqueous layer to extract benezenesulfonyl cyanide, and then the extract and the organic layer were combined, dried over magnesium sulfate, and then methylene chloride was removed by distillation under reduced pressure to obtain 24.8 g (0.15 mol.) of benezenesulfonyl cyanide (yield: 93.8%).

Reference Example 2
<Synthesis of p-toluenesulfonyl cyanide>

The same procedures as those in Reference Example 1 were conducted except for using 34.3 g (0.16 mol.) of sodium p-toluenesulfinate hydrate instead of 32.0 g (0.16 mol.) of sodium benzenesulfinate dihydrate to obtain 27.5 g (0.15 mol.) of p-toluenesulfonyl cyanide (yield: 93.8%).

Reference Example 3
<Production of cyclopentadiene>

Into a 500 ml four-necked flask equipped with a simple distillation device, 300 g (2.27 mol.) of dicyclopentadiene was charged. Dicyclopentadiene was thermally decomposed and distilled while keeping the internal temperature at 155 to 160° C. and the distilling temperature at 50 to 55° C. to obtain 185 g (2.80 mol.) of cyclopentadiene (yield: 61.7%).

Example 1

A large portion of a Teflon tube (inner diameter: 4 mm, length: 2450 mm, and inner volume: 30.8 ml), to which two liquid-feeding pumps were in parallel connected through a "Y"-shaped joint, was immersed into a water bath so that the liquid temperature in the tube could be controlled. The tip of the tube was connected to a 500 ml four-necked flask equipped with a dropping funnel, a pH meter and a thermometer. Into this four-necked flask 130 g of water and 10 g of toluene were charged, and then the flask was cooled to 10° C. or lower. Then, by using two liquid-feeding pumps simultaneously, 164 ml of a solution wherein 103.2 g (0.58 mol.) of benzenesulfonyl cyanide obtained in Reference Example 1 were dissolved in 100 g of methylene chloride at a rate of 0.91 ml/min and 54.0 g (0.80 mol., purity: 99.5%) of cyclopentadiene obtained in Reference Example 3 at a rate of 0.37 ml/min were fed simultaneously in the Teflon tube, and the reaction solution of benzenesulfonyl cyanide and cyclopentadiene mixed in the Teflon tube was added dropwise continuously to the mixed solvent of water and toluene in the flask while stirring. At this time, the residence time of the reaction solution of benzenesulfonyl cyanide and cyclopentadiene mixed inside the Teflon tube was 23 minutes, and the temperature of the water bath to which the Teflon tube was immersed was kept 10° C. or lower. During the continuous addition of the reaction solution of benzenesulfonyl cyanide and cyclopentadiene mixed inside the Teflon tube to the flask, the pH of the reaction mixture was continuously measured simultaneously, and an aqueous solution of 25% sodium hydroxide was added dropwise to the flask to keep the pH of the reaction mixture within a range of 4.4 to 4.6. After the feeding, the temperature of the reaction mixture was kept 10° C. and further the reaction mixture was stirred for 30 minutes. Then, an aqueous solution of 25% sodium hydroxide was added dropwise thereto to adjust the pH of the reaction mixture to 7.5. A portion of this reaction mixture was sampled and subjected to internal standard analysis by HPLC (high performance liquid chromatography) (column: Inertsil ODS-2 (inner diameter: 4.6 mm, length: 150 mm), eluent: 2/8=MeOH/1 mM-$KH_2PO_4$ (adjusted to pH=3.2, using 1M-$H_3PO_4$), flow rate: 1 ml/min, and detection wavelength: UV 225 nm) to find that 60.0 g (0.55 mol.) of 2-azabicyclo[2.2.1]hept-5-en-3-one was present in the reaction mixture (yield: 95.0%).

Example 2

The same procedures as described in Example 1 were conducted except that a solution of 103.2 g (0.58 mol.) of benzenesulfonyl cyanide dissolved in 100 g of o-dichlorobenzene was used instead of the solution wherein 103.2 g (0.58 mol.) of benzenesulfonyl cyanide were dissolved in 100 g of methylene chloride. The resultant reaction mixture was analyzed by HPLC in the same manner as described in Example 1 to find that 59.7 g (0.55 mol.) of 2-azabicyclo[2.2.1]hept-5-en-3-one was obtained (yield: 94.3%).

Example 3

The same procedures as described in Example 1 were conducted except that a solution wherein 105.1 g (0.58 mol.) of p-toluenesulfonyl cyanide were dissolved in 100 g of o-dichlorobenzene were used instead of the solution wherein 103.2 g (0.58 mol.) of benzenesulfonyl cyanide was dissolved in 100 g of methylene chloride. The resultant reaction mixture was analyzed by HPLC in the same manner as described in Example 1 to find that 59.5 g (0.55 mol.) of 2-azabicyclo[2.2.1]hept-5-en-3-one was obtained (yield: 94.0%).

Comparative Example 1

In a 500 ml four-necked flask equipped with a nitrogen flowing tube and a thermometer, 54.0 g (0.80 mol.) of 98.5% cyclopentadiene, 10 g of toluene and 130 g of water were charged, and the inner temperature was controlled to 10° C. Then 103.2 g (0.58 mol.) of 94.3% benzenesulfonyl cyanide were added dropwise thereto from a dropping funnel for about 3 hours while keeping the inner temperature of the flask within the range of 8 to 15° C. During the addition, the pH of the reaction mixture in the flask was continuously measured, and an aqueous solution of 25% sodium hydroxide was added dropwise thereto to keep the pH of the reaction mixture within the range of 4.4 to 4.7. After the addition, the reaction mixture was further stirred at the same temperature for 30 minutes, and an aqueous solution of 25% sodium hydroxide was added dropwise thereto to increase the pH of the reaction mixture to 7.5, and the reaction mixture was transferred into a separatory funnel to separate the aqueous layer. A portion of this aqueous layer was sampled and subjected to internal standard analysis by HPLC in the same manner described in Example 1 with the result that 52.4 g (0.48 mol.) of 2-azabicyclo[2.2.1]hept-5-en-3-one was contained in the layer (yield: 82.8%).

Each reference cited or referred to in this disclosure is incorporated by reference in its entirety. Any patent application to which this application claims priority is also incorporated by reference in its entirety. Specifically, the content of Japanese priority Application No. 124015/1999, filed Apr. 30, 1999 is hereby incorporated in its entirety.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A process for producing 2-azabicyclo[2.2.1]hept-5-en-3-one which comprises:
continuously mixing a substituted sulfonyl cyanide represented by formula (I):

R—SO₂CN             (I), wherein R represents an alkyl group or a phenyl group or a substituted phenyl group, with cyclopentadiene; and then continuously adding the resultant reaction solution to water or to a mixed solvent comprising water and a hydrocarbon solvent under the condition that the pH of the present reaction mixture ranges from 4 to 7.

2. The process of claim 1, wherein the residence time for the continuous mixing of a substituted sulfonyl cyanide represented by formula (I) with cyclopentadiene ranges from 5 to 600 minutes.

3. The process of claim 2, wherein the residence time is within the range from 5 to 120 minutes.

4. The process of claim 2, wherein the residence time is within the range from 10 to 90 minutes.

5. The process of claim 1, wherein the temperature while continuously mixing a substituted sulfonyl cyanide represented by formula (I) with cyclopentadiene is within the range from 0 to 50° C.

6. The process of claim 1, wherein R is an alkyl group selected from the group consisting of methyl, ethyl, n-propyl, i-propyl, n-butyl, i-butyl and t-butyl.

7. The process of claim 1, wherein R is phenyl or a substituted phenyl group having the formula (II):

(II)

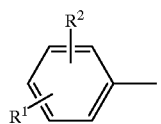

wherein $R^1$ and $R^2$ each independently represent a hydrogen atom, an alkyl group or a halogen atom.

8. The process of claim 1, wherein the hydrocarbon solvent is selected from the group consisting of an aliphatic hydrocarbon, an aromatic hydrocarbon and mixtures thereof.

9. The process of claim 1, wherein the pH ranges from 4 to 6.5.

10. The process of claim 9, where in the pH ranges from 4.2 to 5.5.

11. The process of claim 1, wherein the pH is kept within the range of 4 to 7 by adding an aqueous solution of one or more inorganic alkali compounds to the reaction medium.

12. A process for producing 2-azabicyclo[2.2.1]hept-5-en-3-one, which comprises:

continuously mixing a substituted sulfonyl cyanide represented by formula (I):

$$R\text{—}SO_2CN \qquad (I),$$

wherein R represents an alkyl group or a phenyl group or a substituted phenyl group, with cyclopentadiene; and then continuously adding the resultant reaction solution to water or to a mixed solvent comprising water and a hydrocarbon solvent under conditions where the reaction proceeds with no substantial precipitation of any solid dimerization products.

13. The process of claim 12, wherein the pH of the reaction mixture is maintained within a range from 4 to 7.

14. The process of claim 12, wherein said reaction proceeds without the formation of any solid dimerization products.

* * * * *